US009791415B2

(12) United States Patent
Yang et al.

(10) Patent No.: US 9,791,415 B2
(45) Date of Patent: Oct. 17, 2017

(54) METHOD FOR MONITORING USAGE OF A PHYSICAL VAPOR DEPOSITION (PVD) TARGET WITH AN ULTRASONIC TRANSDUCER

(71) Applicant: Taiwan Semiconductor Manufacturing Co., Ltd., Hsin-Chu (TW)

(72) Inventors: Tsung-Jen Yang, Hsinchu (TW); Cheng-Chieh Chen, Tainan (TW); Hong-Hsing Chou, Jhubei (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 0 days.

(21) Appl. No.: 14/750,148

(22) Filed: Jun. 25, 2015

(65) Prior Publication Data

US 2016/0376695 A1    Dec. 29, 2016

(51) Int. Cl.
| | |
|---|---|
| *C23C 14/00* | (2006.01) |
| *G01N 29/07* | (2006.01) |
| *C23C 14/54* | (2006.01) |
| *G01B 17/02* | (2006.01) |
| *G01N 29/032* | (2006.01) |
| *G01N 29/11* | (2006.01) |
| *C23C 14/34* | (2006.01) |
| *C23C 16/52* | (2006.01) |

(Continued)

(52) U.S. Cl.
CPC ......... *G01N 29/07* (2013.01); *C23C 14/3407* (2013.01); *C23C 14/54* (2013.01); *C23C 16/52* (2013.01); *G01B 17/02* (2013.01); *G01N 29/032* (2013.01); *G01N 29/11* (2013.01); *H01J 37/32935* (2013.01); *H01J 37/3479* (2013.01); *G01N 2291/011* (2013.01); *G01N 2291/015* (2013.01); *G01N 2291/0237* (2013.01); *G01N 2291/02854* (2013.01); *G01N 2291/103* (2013.01); *G01N 2291/2697* (2013.01); *H01J 37/345* (2013.01)

(58) Field of Classification Search
CPC ..................................................... H01J 37/345
See application file for complete search history.

(56) References Cited

U.S. PATENT DOCUMENTS

| | | | | |
|---|---|---|---|---|
| 5,953,827 A | * | 9/1999 | Or | ..................... H01L 21/67098 34/58 |
| 7,566,384 B2 | * | 7/2009 | Cetinkaya | ............... C23C 14/34 204/192.12 |

(Continued)

*Primary Examiner* — Timon Wanga
(74) *Attorney, Agent, or Firm* — Eschweiler & Potashnik, LLC

(57) ABSTRACT

A system for semiconductor manufacturing that uses ultrasonic waves for estimating and monitoring a remaining service lifetime of a consumable element is provided. A consumable element comprises a front side arranged inside a process chamber and a back side, opposite the front side, arranged outside the process chamber. An ultrasonic transducer is arranged on the back side of the consumable element, and directed towards the front side of the consumable element. A monitoring unit is configured to estimate and monitor a remaining service lifetime of the consumable element using the ultrasonic transducer. A method for estimating and monitoring the remaining service lifetime of the consumable element using ultrasonic waves is also provided.

20 Claims, 6 Drawing Sheets

(51) Int. Cl.
*H01J 37/32* (2006.01)
*H01J 37/34* (2006.01)

(56) References Cited

U.S. PATENT DOCUMENTS

| | | | |
|---|---|---|---|
| 7,891,536 B2 | 2/2011 | Hsiao et al. | |
| 2009/0090620 A1* | 4/2009 | Pavloff | C23C 14/3407<br>204/298.13 |

* cited by examiner

METHOD FOR MONITORING USAGE OF A PHYSICAL VAPOR DEPOSITION (PVD) TARGET WITH AN ULTRASONIC TRANSDUCER

BACKGROUND

Physical vapor deposition (PVD) is a process for depositing a thin film of material on a substrate (e.g., a wafer) and is commonly used in the fabrication of semiconductor devices. The PVD process is carried out at a high vacuum in a chamber containing the substrate and a PVD target. During the PVD process, the PVD target is physically converted from a solid into a vapor. The vapor is then transported from the PVD target to the substrate, where it is condensed on the substrate as a thin film.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1A:
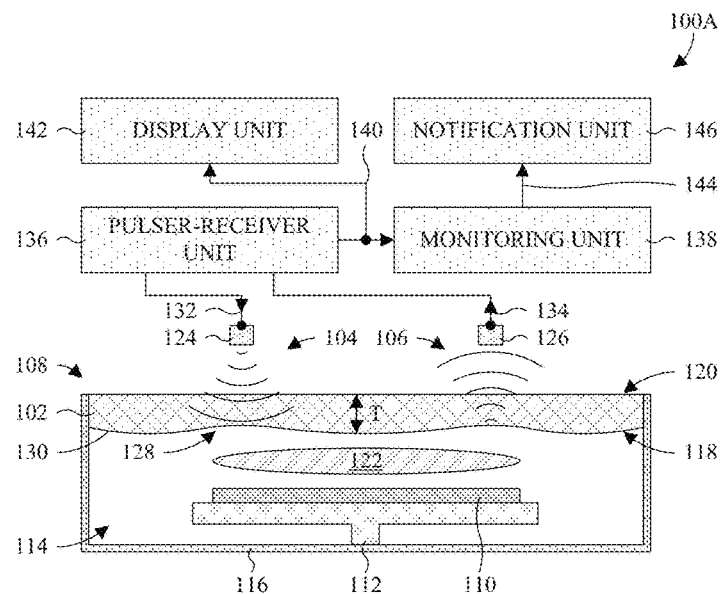
FIG. 1A illustrates a cross-sectional view of some embodiments of a system using ultrasonic waves to monitor a remaining service lifetime of a consumable element.

The present disclosure provides many different embodiments, or examples, for implementing different features of this disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Physical vapor deposition (PVD) targets have finite service lifetimes. Overuse of the PVD targets (i.e., use beyond the service lifetimes) raises reliability and safety concerns. For example, overuse of a PVD target may result in perforation of the PVD target, and process tool arcing. This, in turn, may result in significant production losses, PVD process tool damage, and safety problems. The service lifetimes of PVD targets are commonly estimated by the accumulated energy consumptions (e.g., in kilowatt-hours (kWh)) of the PVD process tools. For example, the service lifetime of a PVD target may be estimated as 100 kWh for the PVD process tool, such that the PVD target reaches its end of life (EOL) when the accumulated energy consumption of the PVD process tool over the life of the PVD target reaches 100 kWh.

While the accumulated energy method to estimating the service lifetimes of PVD targets is common place, it suffers from a number of challenges. Among other things, the accumulated energy method takes time to master and the accuracy of this method depends solely on the hands-on experience of technicians. Further, even when mastered, the estimated service lifetimes of PVD targets are still less than the actual service lifetimes of the PVD targets. It's estimated that approximately 20-40 percent of PVD targets (depending upon the PVD target type) is wasted. The low utilization of PVD targets results in more frequent replacement of PVD targets and more frequent maintenance of the PVD process tools. When PVD targets are replaced, time is needed to retune the PVD process tools for the new PVD targets. The increased replacements and more frequent maintenance, in turn, increase costs and reduce manufacturing throughput. If much of the wasted PVD target material could be utilized, costs would be reduced and throughput could be increased.

In view of the foregoing, the present application is directed to a method for estimating the remaining service lifetimes of PVD targets, as well as a system for carrying out the method. Ultrasonic transducers neighbor the PVD targets and are employed to measure thicknesses of the PVD targets. Since the thicknesses of the PVD targets are proportional to the remaining service lifetimes of the PVD targets, the measurements are used to estimate the remaining service lifetimes of the PVD targets. The method can advantageously be performed in real time and without physical contact with the PVD targets. Further, the method can advantageously measure the thickness of the PVD targets directly and with a high level of accuracy (e.g., with a margin of error less than about 0.01 millimeters). The high level of accuracy leads to more accurate estimates of the remaining service lifetimes of the PVD targets. Collectively, the foregoing advantages lead to improved utilization of the PVD targets, reduced costs, and increased safety.

Beyond PVD targets, the present application is also directed towards a method for estimating the remaining service lifetimes of other consumable elements in process tools, as well as a system for carrying out the method. The other consumable elements are arranged in process chambers and have thicknesses proportional to the remaining service lifetimes of the other consumable elements. For example, the other consumable elements may include ceramic domes used by chemical vapor deposition (CVD) process tools or etch process tools. As with PVD targets, ultrasonic transducers neighbor the other consumable elements and are employed to measure thicknesses of the other consumable elements. The measurements are thereafter used to estimate the remaining service lifetimes of the other consumable elements.

With reference to FIG. 1A, a schematic view 100A of some embodiments of a process system for the manufacture of semiconductor devices is provided. As described in detail hereafter, the system is configured to estimate and monitor a remaining service lifetime of a consumable element 102 using ultrasonic waves 104, 106. The system includes a process tool 108 configured to carry out a semiconductor manufacturing process on a wafer 110. The process tool 108 may be, for example, a CVD process tool, a PVD process tool, an etch process tool, or a cluster process tool combining multiple semiconductor manufacturing processes. The process tool 108 includes a wafer support 112 arranged within a process chamber 114, and configured to support the wafer 110. The process chamber 114 is at least partially defined by the consumable element 102 and a housing 116. In some embodiments, during use of the process tool 108, the process chamber 114 has a pressure and/or a temperature that are elevated relative to a pressure and/or a temperature of the ambient environment of the process tool 108.

The consumable element 102 may be, for example, a PVD target, a CVD dome, or an etch dome, and includes a thickness T. The thickness T of the consumable element 102 is proportional to a remaining service lifetime of the consumable element 102, and extends from a front side 118 of the consumable element 102 to a back side 120 of the consumable element 102 that is opposite the front side 118. The front side 118 of the consumable element 102 is arranged inside the process chamber 114, and the back side 120 of the consumable element 102 is arranged outside the process chamber 114. As the process tool 108 is used, the front side 118 of the consumable element 102 is eroded towards the back side 120 of the consumable element 102. For example, the front side 118 of the consumable element 102 may be eroded by plasma 122 in the process chamber 114.

One or more ultrasonic transducers 124, 126 are arranged on the back side 120 of the consumable element 102, spaced from the consumable element 102. The ultrasonic transducer(s) 124, 126 are focused or otherwise directed towards the front side 118 of the consumable element 102, typically towards regions 128 on the front side 118 of the consumable element 102 that erode fastest during use of the process tool 108. The regions 128 on the front side 118 of the consumable element 102 that erode fastest tend to be the thinnest and hence the most relevant for monitoring the remaining service lifetime of the consumable element 102. The ultrasonic transducer(s) 124, 126 further have focal lengths with working ranges that reach a surface 130 on the front side 118 of the consumable element 102 that is at an interface between the front side 118 of the consumable element 102 and the process chamber 114.

The ultrasonic transducer(s) 124, 126 include a set of one or more transmitting ultrasonic transducers 124 and a set of one or more receiving ultrasonic transducer 126. In some embodiments, the transmitting set and the receiving set partially or fully overlap. Further, in some embodiments, the transmitting set and the receiving set are mutually exclusive. The transmitting ultrasonic transducer(s) 124 are configured to receive one or more corresponding driver signals 132 carrying electrical pulses, and to transmit ultrasonic waves 104 representing the electrical pulses towards the front side 118 of the consumable element 102. The receiving ultrasonic transducer(s) 126 are configured to receive ultrasonic waves, including reflections 106 of the transmitted ultrasonic waves 104 off the front side surface 130 of the consumable element 102. As is known in the art, ultrasonic waves reflect at boundaries between materials with different acoustic impedances. Further, the receiving ultrasonic transducer(s) 126 are configured to generate one or more corresponding sensor signal(s) 134 carrying electrical pulses representing the received ultrasonic waves 106.

A pulser-receiver unit 136 is electrically coupled with the ultrasonic transducer(s) 124, 126, via one or more communication channels corresponding to the ultrasonic transducer(s) 124, 126. In some embodiments, the pulser-receiver unit 136 includes multiple communication channels individual to the ultrasonic transducer(s) 124, 126. Further, in some embodiments, the pulser-receiver unit 136 includes at least one communication channel individual to the transmitting ultrasonic transducer(s) 124 and at least one communication channel individual to the receiving ultrasonic transducer(s) 126.

The pulser-receiver unit 136 is configured to generate one or more driver signals 132 carrying electrical pulses, and to transmit the driver signal(s) 132 to corresponding ones of the transmitting ultrasonic transducer(s) 124. Further, the pulser-receiver unit 136 is configured to generate the electrical pulses in response to measurement events. The measurement events may be, for example, periodic timer events (e.g., a timer event every 5 seconds) or an external event (e.g., an event triggered by a user input device or by a monitoring unit 138). The electrical pulses trigger the transmitting ultrasonic transducer(s) 124 to transmit ultrasonic waves 104 towards the front side 118 of the consumable element 102. Further, the pulser-receiver unit 136 is configured to receive one or more sensor signals 134 from corresponding ones of the receiving ultrasonic transducer(s) 126, to encode the signal(s) 134, and to transmit the one or more encoded signals 140 to a display unit 142 and/or the monitoring unit 138. The sensor signal(s) 134 carry electrical pulses representing ultrasonic waves 106 received by the receiving ultrasonic transducer(s) 126. The sensor signal(s) 134 may be encoded by, for example, sampling the amplitude of the signal(s) 134 (i.e., periodically converting the amplitudes of the signal(s) 134 to numbers) or otherwise digitally encoding the sensor signal(s) 134, and/or may be transferred by, for example, RS-232, Internet Protocol (IP), or some other communications protocol.

The pulser-receiver unit 136 includes hardware and, in some embodiments, software configured to carry out the foregoing functionality. For example, the pulser-receiver unit 136 may include an analog-to-digital converter (ADC), a field-programmable gate array (FPGA), or some other circuit. Further, to the extent that the pulser-receiver unit 136 includes software, the pulser-receiver unit 136 includes at least one processor configured to execute the software. For example, the pulser-receiver unit 136 may include a microcontroller, a microprocessor, or an application-specific integrated circuit (ASIC) configured to execute the software.

The display unit 142 and/or the monitoring unit 138 are electrically coupled to the pulser-receiver unit 136, and configured to receive the encoded sensor signal(s) 140 from the pulser-receiver unit 136. Further, in some embodiments, the display unit 142 and/or the monitoring unit 138 are further configured to filter noise from the encoded sensor signal(s) 140. For example, a low pass or high pass filter may be used to filter noise from the encoded sensor signal(s) 140. Using the encoded/filtered sensor signal(s), the display unit 142 is configured to display the signal(s) for visual inspection. The display unit 142 may be, for example, an oscilloscope. Using the encoded/filtered sensor signal(s), the monitoring unit 138 is configured to estimate and monitor the remaining service lifetime of the consumable element 102. Where multiple encoded/filter sensor signal(s) are present, the signal(s) may be averaged or otherwise combined before use and/or processing (as described below) by the monitoring unit 138. Alternatively, where multiple encoded/filter sensor signal(s) are present, the signal(s) may be individually used and/or processed (as described below) by the monitoring unit 138.

To estimate the remaining service lifetime of the consumable element 102, the monitoring unit 138 waits for the start of a measurement event or otherwise triggers the start of a measurement event. Typically, measurement events occur continuously and/or periodically so as to estimate the remaining service lifetime of the consumable element in real time or near real time. In some embodiments, the monitoring unit 138 identifies the start of the measurement event by the encoded/filtered sensor signal(s) exceeding a noise threshold demarcating noise from the measurement event. The noise threshold may be observed from the steady state noise level of the encoded/filtered sensor signal(s). In other embodiments, the monitoring unit 138 identifies the start of a measurement event based on a signal from the trigger (e.g., a user input device) of the measurement event.

In response to the start of a measurement event, the monitoring unit 138 measures a reflection time for the transmitted ultrasonic wave 104 of the measurement event using the encoded/filtered sensor signal(s). The reflection time is the time it takes for the transmitted ultrasonic wave 104 to traverse the thickness T of the consumable element 102 from the transmitting ultrasonic transducer(s) 124 to the front side surface 130 of the consumable element 102, and for a reflection 106 of the ultrasonic wave 104 to traverse the thickness T of the consumable element 102 from the front side surface 130 of the consumable element 102 to the receiving ultrasonic transducer(s) 126. The reflection time is proportional to the remaining service lifetime of the consumable element 102, and is therefore an indirect estimate of the remaining service lifetime of the consumable element 102.

The encoded/filtered sensor signal(s) carry an electrical pulse representing the reflection 106 of the transmitted ultrasonic wave 104. Therefore, the reflection time is measured as the time difference between the start of the measurement event and the pulse for the reflection 106 of the transmitted ultrasonic wave 104. In some embodiments, the encoded/filtered sensor signal(s) further carry a pulse representing the transmitted ultrasonic wave 104. In such embodiments, the reflection time is measured as the time difference between the pulses for the transmitted ultrasonic wave 104 and the reflection 106 of the transmitted ultrasonic wave 104. For example, the reflection time for the transmitted ultrasonic wave may be measured by graphing the strength of the encoded/filtered sensor signal(s) (e.g., in decibels) over time. Early in time, the graph will include a first peak representing the transmitted ultrasonic wave 104. Later in time, and immediately neighboring the first peak, the graph will include a second peak representing the reflection 106 of the transmitted ultrasonic wave 104. After graphing the encoded/filtered sensor signal(s), the first and second peaks are identified in the graph and the reflection time is measured as the time difference between the first and second peaks.

In some embodiments, after measuring the reflection time, the monitoring unit 138 further transforms the reflection time to a different quantity that is proportional to or inversely proportional to the remaining service lifetime of the consumable element 102. For example, the reflection time may be transformed into an estimate of the thickness T of the consumable element 102, which is an indirect estimate of the remaining service lifetime of the consumable element 102. As another example, the reflection time may be transformed into a direct estimate of the remaining service lifetime of the consumable element 102. In some embodiments, the transform is a linear transform, and/or is determined by modeling the relationship between reflection time and the variable to which reflection time is transformed using a machine learning algorithm, such as linear regression. For example, the transform for thickness may be $T'=0.5(R*S)$, where $T'$ is the thickness estimate, R is the reflection time, and S is the known speed of ultrasonic waves within the material of the consumable element 102.

To monitor the remaining service lifetime of the consumable element 102, the monitoring unit 138 compares reflection times, or transformations thereof, to a threshold representative of the EOL of the consumable element 102. The threshold may be, for example, determined through observation of test samples or previous consumable elements. If a comparison indicates that the consumable element 102 has reached its EOL, an EOL signal 144 may be generated and transmitted to a notification unit 146, thereby alerting a user of the process tool 108 that the consumable element 102 has reached its EOL. The notification unit 146 may be, for example, an audio and/or visual device, such as a light source, or a software module. In some embodiments, the notification unit 146 and the display unit 142 are one and the same.

Advantageously, the foregoing monitoring of the consumable element 102 can be performed in real time and without physical contact with the consumable element 102 during use of the process tool 108. For example, the measurement events can be continuously triggered during the use of the process tool 108. Further, the foregoing monitoring advantageously determines the remaining service lifetime of the consumable element 102 with a high level of accuracy, thereby allowing increased usage of the consumable element 102, improved safety, reduced costs, and increased throughput.

In some embodiments, the monitoring unit 138 is further configured to display a graph of reflection times, or transformations thereof, on the display unit 142 or some other display unit. For example, the reflection times or estimates of the thickness T of the consumable element 102 may be graphed and displayed over time. This advantageously allows trends to be observed and high-wear uses to be identified (i.e., uses that disproportionately wear the consumable element 102).

In some embodiments, the monitoring unit 138 is further configured to estimate and display a profile of the front side surface 130 on the display unit 142 or some other display unit. For example, the profile estimates may be displayed over time, thereby allowing a user of the process tool 108 to advantageously observe wear of the consumable element 102. The embodiments, may be used where the ultrasonic transducer(s) 124, 126 include multiple ultrasonic transducers, such as 10 or 20 ultrasonic transducers, spread across the front side surface 130, typically uniformly. Further, the embodiments may be implemented by mapping the individual reflection times for the ultrasonic transducer(s) 124, 126 to a two dimensional plane corresponding to the front side surface 130 and, in some embodiments, interpolating reflection times between measured reflection times.

The monitoring unit 138 includes hardware and, in some embodiments, software configured to carry out the foregoing functionality. For example, the monitoring unit 138 may include a FPGA or some other circuit. Further, to the extent that the monitoring unit 138 includes software, the monitoring unit 138 includes at least one processor configured to execute the software. For example, the monitoring unit 138 may include a microcontroller, a microprocessor, or an ASIC configured to execute the software.

In some embodiments, the functionalities of the pulser-receiver unit 136 and the monitoring unit 138 are combined in to a common operating unit. Further, in some embodiments, some of the functionalities of the monitoring unit 138 are shifted to the pulser-receiver unit 136 or some other operational unit, and/or some of the functionalities of the pulser-receiver unit 136 are shifted to the monitoring unit 138 or some other operational unit. Even more, in some embodiments, some or all of the functionalities of the pulser-receiver unit 136 and/or the monitoring unit 138 are shifted into the process tool 108.

Figure 1B:
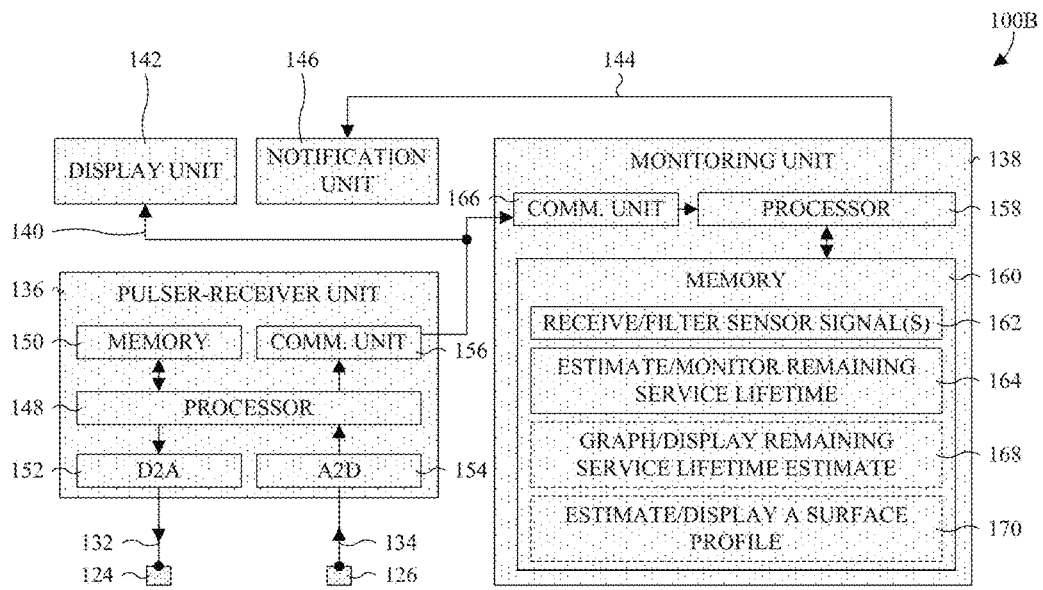
FIG. 1B illustrates a block diagram of some embodiments of a pulser-receiver unit and a monitoring unit of the system of FIG. 1A.

With reference to FIG. 1B, a block diagram 100B of some embodiments of the pulser-receiver unit 136 and the monitoring unit 138 is provided. The pulser-receiver unit 136 includes at least one processor 148 executing processor executable instructions stored on at least one memory 150. The processor executable instructions instruct the at least one processor 148 to generate the driver signal(s) 132 using one or more digital-to-analog converters (DACs) 152 corresponding to the transmitting ultrasonic transducer(s) 124. The DAC(s) 152 generate the driver signal(s) 132 in response to digital input from the at least one processor 148. The processor executable instructions further instruct the at least one processor 148 to receive the sensor signal(s) 134, encode the sensor signal(s) 134, and transmit the sensor signal(s) 134 to the monitoring unit 138.

The at least one processor 148 receives and encodes the sensor signal(s) 134 using one or more analog-to-digital converters (ADCs) 154 corresponding to the receiving ultrasonic transducer(s) 126. The ADC(s) 154 convert the sensor signal(s) 134 to digital data (i.e., digitally encode the sensor signal(s) 134) for the at least one processor 148. Further, the at least one processor 148 transmits the encoded sensor signal(s) 140 to the monitoring unit 138 using a communication unit 156. The communication unit 156 may, for example, transmit the encoded sensor signal(s) using a serial interface, such as RS-232, or data packets, such as IP.

The monitoring unit 138 includes at least one processor 158 executing processor executable instructions stored on at least one memory 160. The processor executable instructions include a receive module 162 and a monitor module 164. The receive module 162 instructs the at least one processor 158 to receive the encoded sensor signal(s) 140 using a communication unit 166 and, in some embodiments, to filter the encoded sensor signal(s) 140. The communication unit 166 may, for example, receive the encoded sensor signal(s) 140 using RS-232 or IP. The monitor module 164 instructs the at least one processor 158 to estimate the remaining service lifetime of the consumable element 102 from the encoded/filtered sensor signal(s), and to monitor the remaining service lifetime estimate.

In some embodiments, the processor executable instructions further include a graph module 168 and/or a surface profile module 170. The graph module 168 instructs the at least one processor 158 to graph and display the remaining service lifetime estimate over time on the display unit 142 or some other display unit. The surface profile module 170 instructs the at least one processor 158 to estimate and display a profile of the front side surface 130 on the display unit 142 or some other display unit.

Figure 2:
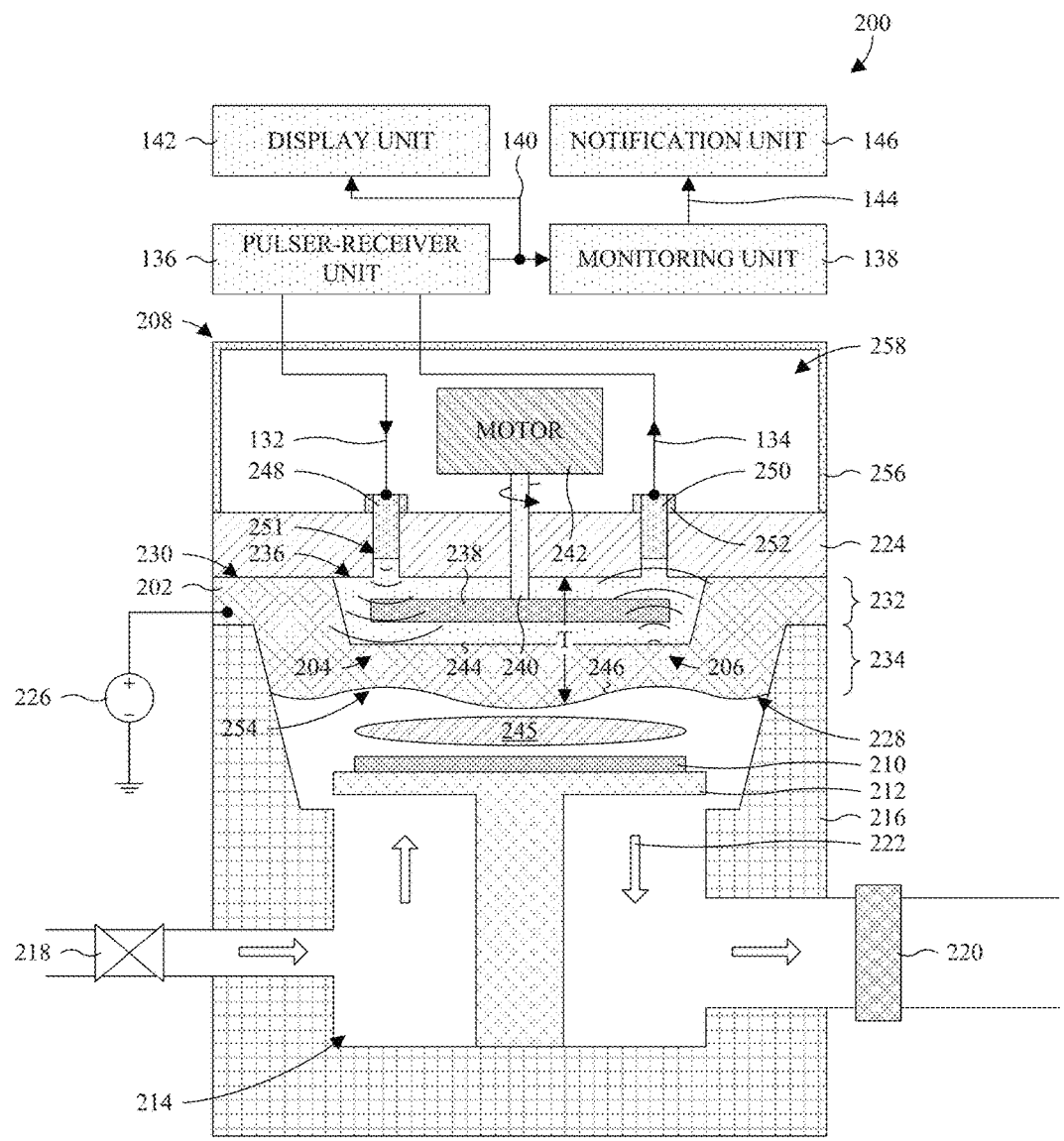
FIG. 2 illustrates a cross-sectional view of some embodiments of a system using ultrasonic waves to monitor a remaining service lifetime of a PVD target.

With reference to FIG. 2, a cross-sectional view 200 of some embodiments of a PVD system for the manufacture of semiconductor devices is provided. As described in detail hereafter, the system is configured to estimate and monitor a remaining service lifetime of a PVD target 202, typically in real time, using ultrasonic waves 204, 206. The system includes a PVD process tool 208 configured to carry out a PVD process on a wafer 210. The PVD process tool 208 includes a wafer support 212 arranged within a process chamber 214, and configured to support the wafer 210. The process chamber 214 is defined at least partially by the PVD target 202 and a lower housing 216 underlying the PVD target 202. In some embodiments, the process chamber 214 is coupled to a gas valve 218 and/or an exhaust pump 220 configured to facilitate the flow of gas 222 respectively into and out of the process chamber 214.

The PVD target 202 underlies a back plate 224 and is removably mounted to the back plate 224. Typically, the PVD target 202 shares a footprint with the back plate 224. Further, in some embodiments, the PVD target 202 is electrically coupled to a power source 226, such as a voltage source. The PVD target 202 is a consumable piece of a source material (i.e., a consumable element) that is consumed from a front side 228 of the PVD target 202 to a back side 230 of the PVD target 202 that is opposite the front side 228. Typically, a thickness T of the PVD target 202 varies laterally due to uneven consumption of the source material. In some embodiments, the thickness T of the PVD target 202 is about 30-70 millimeters, such as about 60 millimeters. The source material may be, for example, nickel (Ni), nickel platinum (NiPt) alloys, nickel titanium (NiTi) alloys, cobalt (Co), aluminum (Al), copper (Cu), titanium (Ti), tantalum (Ta), tungsten (W), indium tin oxide (ITO), zinc sulfide-silicon dioxide (ZnS—$SiO_2$), gold (Au), silver (Ag), and other noble metals.

In some embodiments, the PVD target 202 includes a base region 232 and a protruding region 234. The base region 232 overlies the protruding region 234, along the back side 230 of the PVD target 202. Typically, the base region 232 has a generally uniform thickness and/or width. For example, the base region 232 may have a thickness of about 30-50 millimeters, such as about 40 millimeters. The protruding region 234 underlies the base region 232, along the front side 228 of the PVD target 202, and protrudes from the base region 232. Typically, the protruding region 234 has a varying thickness and/or a tapering width. For example, the protruding region 234 may have a thickness varying around 10-30 millimeters. Footprints of the base and protruding regions 232, 234 may be the same or different shapes, but the footprint of the protruding region 234 is typically smaller (e.g., by area and/or dimensions) than that of the base region 232. The footprints may be any suitable shapes, such as, for example, circles, squares, rectangles, ovals, triangles, polygons, and so on. Further, centers of the base and protruding regions 232, 234 are typically vertically aligned with one another.

Further, in some embodiments, the PVD target 202 includes a magnetron opening 236 on the back side 230 of the PVD target 202 that is sealed by the back plate 224. The magnetron opening 236 accommodates a magnetron 238 suspended and rotated within the magnetron opening 236 by a shaft 240 extending through the back plate 224 to a motor 242 overlying the back plate 224. Typically, the shaft 240 rotates about an axis that extends vertically through a center of the back plate 224. The magnetron opening 236 is further filled around the magnetron and shaft with a fluid 244. The fluid 244 may be, for example, water, such as deionized water, and is typically circulated through an inlet and an outlet (not shown) in the back plate 224 by a pump (not shown). Circulating the fluid 244 advantageously allows heat generated by the magnetron 238 to be removed from the magnetron opening 236.

During use of the PVD process tool 208, any number of PVD processes may be used. For example, sputtering, evaporation, or electron beam evaporation may be used. However, in some embodiments, during use of the PVD process tool 208, the exhaust pump 220 may be used to remove any existing gas in the process chamber 214, such as oxygen and nitrogen. Further, the gas valve 218 may be used to fill the process chamber with a gas, such as argon or some other inert gas, and a high voltage, such as a high direct current (DC) voltage, may applied to the PVD target 202 by the power source 226. The gas, together with the high voltage, creates plasma 245 in the process chamber 214 and the high voltage accelerates ions of the plasma 245 towards a surface 246 on the front side 228 of the PVD target 202. When the ions strike the front side surface 246 of the PVD target 202, source material is ejected or sputtered towards the wafer 210. Where the magnetron 238 is present, the magnetic fields from the magnetron 238 direct the ejected or sputtered source material to the wafer 210.

One or more ultrasonic transducers 248, 250 are mounted to the back plate 224, over the PVD target 202 and the back plate 224. The ultrasonic transducer(s) 248, 250 partially fill one or more corresponding transducer openings 251 in the back plate 224. The transducer opening(s) 251 extend vertically through the back plate 224, such that the ultrasonic transducer(s) 248, 250 have direct paths to the PVD target 202. Further, in some embodiments, where the magnetron 238 is present, the transducer opening(s) 251 are arranged over the magnetron opening 236, such that the ultrasonic transducer(s) 248, 250 are in direct fluid communication with the fluid 244. One or more seals 252, typically ring-shaped seals, may be arranged over the back plate 224, laterally surrounding the ultrasonic(s) transducers 248, 250 and the transducer opening(s) 251, to prevent fluid from escaping from the magnetron opening 236 through the transducer opening(s) 251.

The ultrasonic transducer(s) 248, 250 are focused or otherwise directed towards the front side 228 of the PVD target 202, typically towards regions 254 on the front side 228 of the PVD target 202 that erode fastest during use of the PVD process tool 208. For example, where the magnetron 238 is present, the PVD target 202 is focused towards regions on the front side 228 of the PVD target 202 with the strongest magnetic field. Further, the ultrasonic transducer(s) 248, 250 further have focal lengths with working ranges that reach the front side surface 246 of the PVD target 202. In some embodiments, where the PVD target 202 has a thickness of about 40-60 millimeters, the ultrasonic transducer(s) 248, 250 have focal lengths of about 50 millimeters with working ranges of about 30-70 millimeters.

The ultrasonic transducer(s) 248, 250 include a set of one or more transmitting ultrasonic transducers 248 and a set of one or more receiving ultrasonic transducers 250. The transmitting ultrasonic transducer(s) 248 are configured to receive one or more corresponding driver signals 132 carrying electrical pulses, and to transmit ultrasonic waves 204 representing the electrical pulses towards the front side 228 of the PVD target 202. The receiving ultrasonic transducer(s) 250 are configured to receive ultrasonic waves, including reflections 206 of the transmitted ultrasonic waves 204 off the front side surface 246 of the PVD target 202. Further, the receiving ultrasonic transducer(s) 250 are configured to generate one or more corresponding sensor signal(s) 134 carrying electrical pulses representing the received ultrasonic waves 206.

In some embodiments, an upper housing 256 is arranged over the back plate 224 to define a cavity 258 between the back plate 224 and the upper housing 256. The cavity 258 includes the ultrasonic transducer(s) 248, 250 and, in some embodiments, the motor 242, whereby the upper housing 256 advantageously protects the ultrasonic transducer(s) 248, 250 and, in some embodiments, the motor 242. The cavity 258 is typically maintained at a room temperature and/or at 1 atmosphere (atm) of pressure.

A pulser-receiver unit 136 is electrically coupled with the ultrasonic transducer(s) 248, 250, via one or more communication channels corresponding to the ultrasonic transducer(s) 248, 250. The pulser-receiver unit 136 is configured to generate one or more driver signals 132 carrying electrical pulses, and to transmit the driver signal(s) 132 to corresponding ones of the transmitting ultrasonic transducer(s) 248. Further, the pulser-receiver unit 136 is configured to receive one or more sensor signals 134 from corresponding ones of the receiving ultrasonic transducer(s) 250, to encode the signal(s), and to transmit the one or more encoded signals 140 to a display unit 142 and/or a monitoring unit 138.

The display unit 142 and/or the monitoring unit 138 are electrically coupled to the pulser-receiver unit 136, and configured to receive the encoded sensor signal(s) 140 from the pulser-receiver unit 136. Further, in some embodiments, the display unit 142 and/or the monitoring unit 138 are further configured to filter noise from the encoded sensor signal(s) 140. Using the encoded/filtered sensor signal(s), the display unit 142 is configured to display the signal(s) for visual inspection. Using the encoded/filtered sensor signal(s), the monitoring unit 138 is configured to estimate and monitor the remaining service lifetime of the PVD target 202. If the monitoring unit 138 detects that that the PVD target 202 has reached its EOL, an EOL signal 144 may be generated and transmitted to a notification unit 146.

Figure 3A:
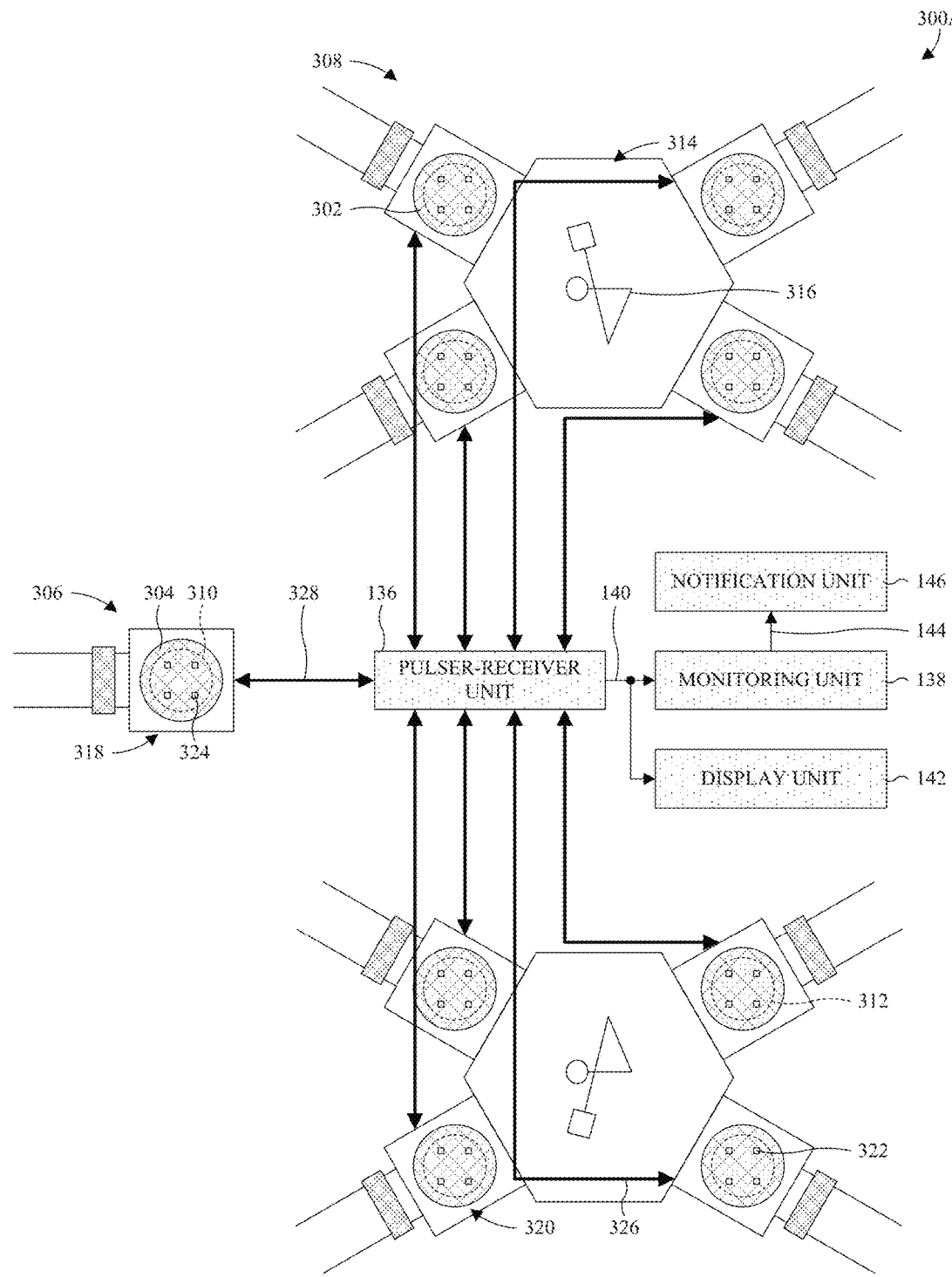
FIG. 3A illustrates a top view of some embodiments of a system using ultrasonic waves to monitor remaining service lifetimes of multiple consumable elements.

With reference to FIG. 3A, top view 300A of some embodiments of a system for the manufacture of semiconductor devices is provided. As described in detail hereafter, the system is configured to estimate and monitor remaining service lifetimes of multiple consumable elements 302, 304, typically in real time, using ultrasonic waves (not shown). The system includes one or more process tools 306, 308 within which the consumable elements 302, 304 are arranged. The process tool(s) 306, 308 may include one or more single-chamber process tools 306 and/or one or more multi-chamber process tools 308 (i.e., cluster process tools). A single-chamber process tool 306 is limited to a single process chamber 310, whereas a multi-chamber process tool 308 includes multiple process chambers 312, typically arranged around a central chamber 314 accommodating a robot 316 configured to move wafers between the multiple process chambers 312. The process chambers 310, 312 of the process tool(s) 306, 308 correspond to the consumable elements 302, 304, typically with a 1 to 1 correspondence, and are partially defined by the consumable elements 302, 304. The process chambers 310, 312 of the process tool(s) 306, 308 may be, for example, configured for PVD, CVD, or etching.

The consumable elements 302, 304 have thicknesses that are proportional to remaining service lifetimes of the consumable elements 302, 304. The thicknesses extend from front sides (not shown) of the consumable elements 302, 304 to back sides 318, 320 of the consumable elements 302, 304 that are opposite the front sides. The front sides of the consumable elements 302, 304 are arranged inside the process chambers 310, 312, and the back sides 318, 320 of the consumable elements 302, 304 are arranged outside the process chambers 310, 312. As the process tool(s) 306, 308 are used, the front sides of the consumable elements 302, 304 are eroded towards the back sides 318, 320 of the consumable elements 302, 304. The consumable elements 302, 304 may be, for example, PVD targets, CVD domes, or etch domes.

Ultrasonic transducers 322, 324 are arranged on the back sides 318, 320 of the consumable elements 302, 304, spaced from the consumable elements 302, 304. The ultrasonic transducers 322, 324 are focused or otherwise directed towards the front sides of the consumable elements 302, 304, typically towards regions on the front sides of the consumable elements 302, 304 that erode fastest during use of the process tool(s) 306, 308. The ultrasonic transducers 322, 324 further have focal lengths with working ranges that reach surfaces on the front sides of the consumable elements 302, 304 that are at interfaces between the front sides of the consumable elements 302, 304 and the process chambers 310, 312.

The ultrasonic transducers 322, 324 include, for each one of the consumable elements 302, 304, a set of one or more transmitting ultrasonic transducers 322 and a set of one or more receiving ultrasonic transducers 324. The transmitting and receiving sets may be overlapping or mutually exclusive. The transmitting ultrasonic transducers 322 are configured to receive corresponding driver signals carrying electrical pulses from a pulser-receiver unit 136, and to transmit ultrasonic waves representing the electrical pulses towards the front sides of the consumable elements 302, 304. The receiving ultrasonic transducers 324 are configured to receive ultrasonic waves, including reflections of the transmitted ultrasonic waves off the front side surfaces of the consumable elements 302, 304. Further, the receiving ultrasonic transducers 324 are configured to transmit corresponding sensor signals carrying electrical pulses representing the received ultrasonic waves to the pulser-receiver unit 136.

The pulser-receiver unit 136 is electrically coupled with the ultrasonic transducers 322, 324 via multiple communication channels 326, 328 corresponding to the consumable elements 302, 304 and/or the process tools 306, 308. In some embodiments, the multiple communication channels 326, 328 are individual to the consumable elements 302, 304 and/or the process tools 306, 308. Further, in some embodiments, the multiple communication channels 326, 328 are individual to the transmitting and receiving sets. The pulser-receiver unit 136 is configured to generate driver signals carrying electrical pulses, and to transmit the driver signals to corresponding ones of the transmitting ultrasonic transducers 322 over the communication channels 326, 328. Further, the pulser-receiver unit 136 is configured to receive sensor signals over the communication channels 326, 328 from corresponding ones of the receiving ultrasonic transducers 324, to encode the signals, and to transmit the encoded signals 140 to a display unit 142 and/or a monitoring unit 138.

The display unit 142 and/or the monitoring unit 138 are electrically coupled to the pulser-receiver unit 136, and configured to receive the encoded sensor signals 140 from the pulser-receiver unit 136. Further, in some embodiments, the display unit 142 and/or the monitoring unit 138 are further configured to filter noise from the encoded sensor signals 140. Using the encoded/filtered sensor signals, the display unit 142 is configured to display the signals for visual inspection. Using the encoded/filtered sensor signals, the monitoring unit 138 is configured to estimate and monitor the remaining service lifetimes of the consumable elements 302, 304. If the monitoring unit 138 detects that a consumable element 302, 304 has reached its EOL, an EOL signal 144 may be generated and transmitted to a notification unit 146.

Figure 3B:
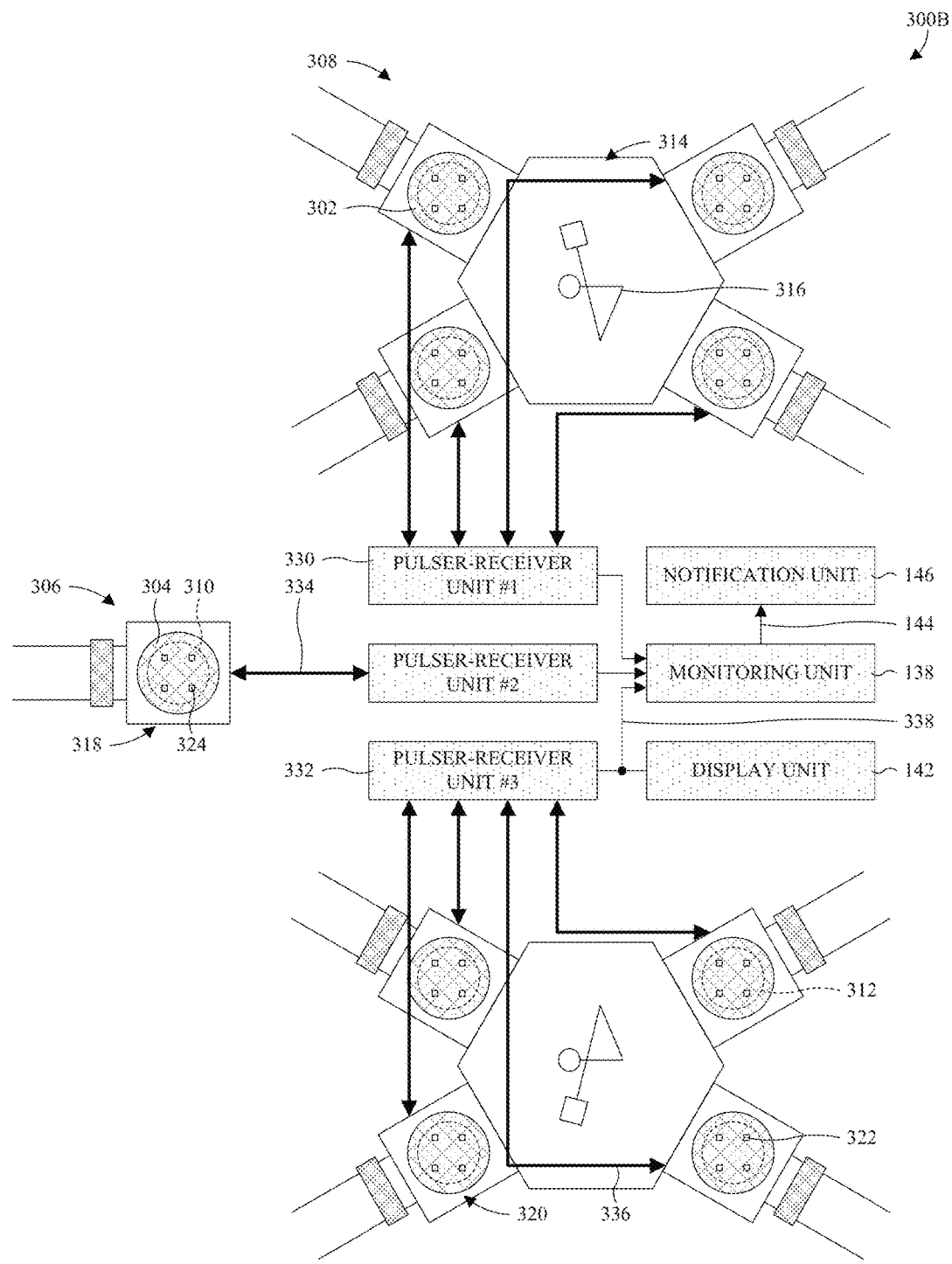
FIG. 3B illustrates a top view of other embodiments of the system of FIG. 3A.

With reference to FIG. 3B, a top view 300B of alternative embodiments of the system of FIG. 3A is provided. In contrast with the embodiments of FIG. 3A, a plurality of pulser-receiver units 330, 332 are electrically coupled with the ultrasonic transducers 322, 324 via multiple communication channels 334, 336 corresponding to the consumable elements 302, 304 and/or the process tools 306, 308. The pulser-receiver units 330, 332 are configured to generate driver signals carrying electrical pulses, and to transmit the driver signals to corresponding ones of the transmitting ultrasonic transducers 322 over the communication channels 334, 336. Further, the pulser-receiver unit 330, 332 are configured to receive sensor signals from corresponding ones of the receiving ultrasonic transducers 324 over the communication channels 334, 336, to encode the signals, and to transmit the encoded signals 338 to the display unit 142 and/or the monitoring unit 138.

Figure 4:
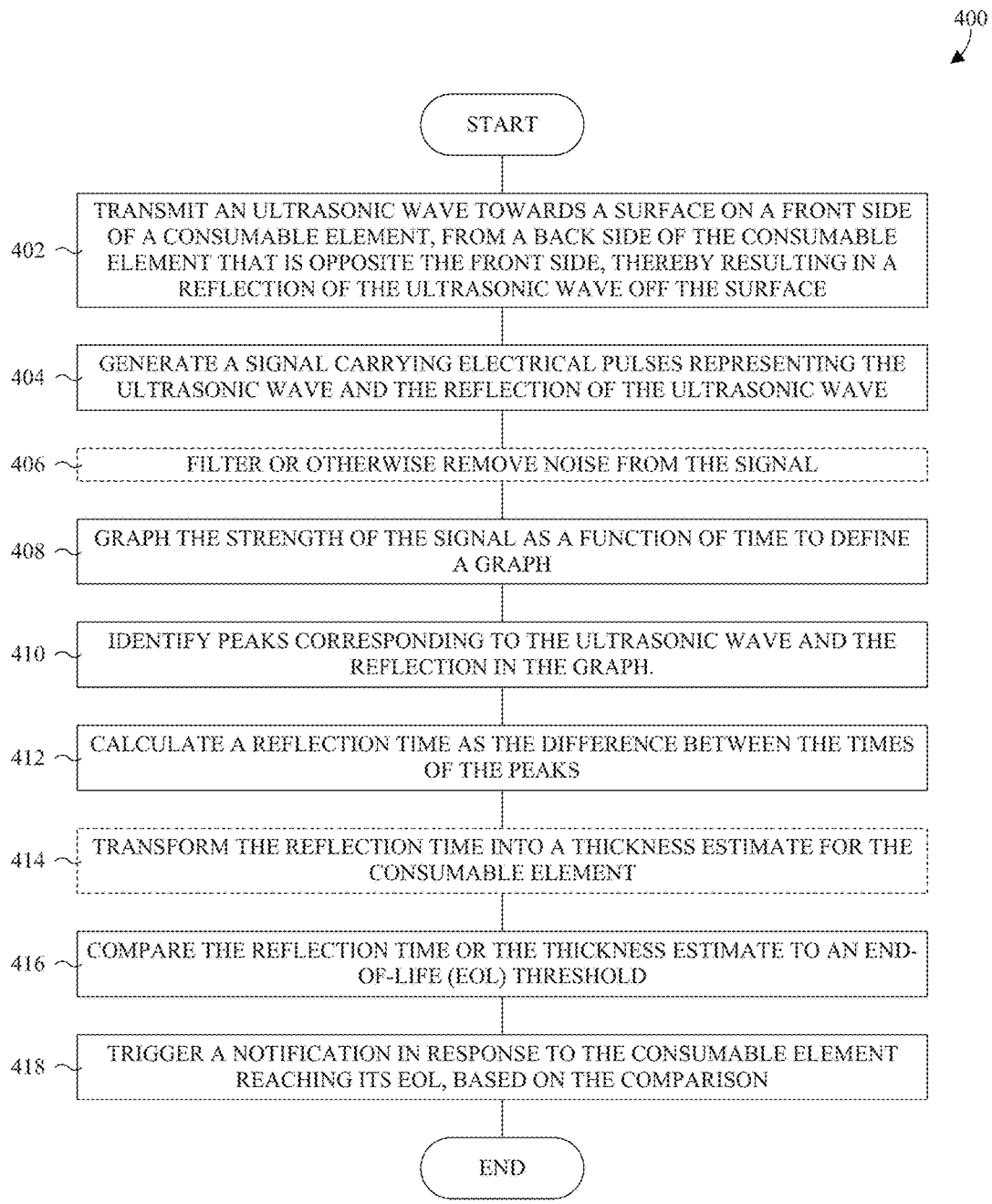
FIG. 4 illustrates a flowchart of some embodiments of a method for monitoring a remaining service lifetime of a consumable element using ultrasonic waves.

With reference to FIG. 4, a flowchart 400 of some embodiments of a method for estimating and monitoring a remaining service lifetime of a consumable element using ultrasonic waves is provided. The method may be employed within the systems of FIGS. 1A & B, 2, 3A & B and is typically performed continuously or repeatedly for real time or near real time monitoring of the consumable element.

At 402, an ultrasonic wave is transmitted towards a surface on a front side of a consumable element, from a back side of the consumable element that is opposite the front side, thereby resulting in a reflection of the ultrasonic wave off the front side surface.

At 404, a signal is generated carrying electrical pulses representing the ultrasonic wave and the reflection of the ultrasonic wave.

At 406, in some embodiments, noise is filtered or otherwise removed from the signal.

At 408, strength of the signal is graphed as a function of time to define a graph.

At 410, peaks corresponding to the ultrasonic wave and the reflection are identified in the graph.

At 412, a reflection time is calculated as the difference between the times of the peaks.

At 414, in some embodiments, the time difference is translated into a thickness estimate for the consumable element.

At 416, the reflection time or the thickness estimate are compared to an EOL threshold.

At 418, a notification is triggered in response to the consumable element reaching its EOL, based on the comparison.

In alternative embodiments, at 404, the signal is restricted to an electrical pulse for the reflection of the ultrasonic wave. In such embodiments, Acts 408, 410, 412 are as described above, except that an electrical pulse for the ultrasonic wave is not used to identify the time of the ultrasonic wave. Instead, other means are used to identify the time of the ultrasonic wave. For example, a signal triggering the transmission of the ultrasonic wave may be used to identify the time of the ultrasonic wave.

Advantageously, the method can be performed in real time and without physical contact with the consumable element. Further, the method can advantageously measure the reflection time and the thickness of the consumable element with a high level of accuracy (e.g., with a margin of error less than about 0.01 millimeters). Since the reflection time and the thickness estimate are proportional to the remaining service lifetime of the consumable element, the high level of accuracy advantageously leads to more accurate estimates of the remaining service lifetimes of the consumable element. Collectively, the foregoing advantages lead to improved utilization of the consumable element, reduced costs, and increased safety.

Figure 5A:
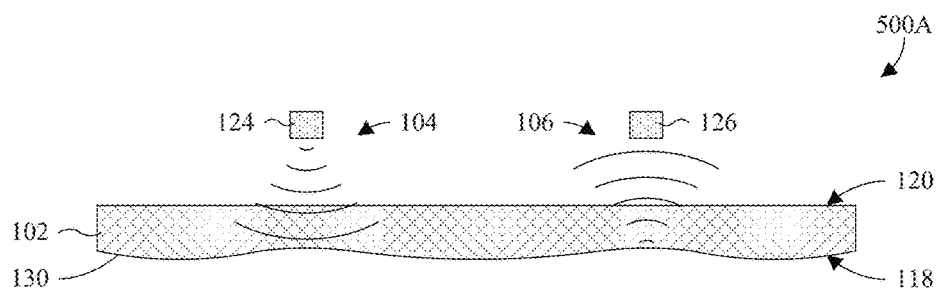
FIG. 5A illustrates a cross-sectional view of some embodiments of a consumable element during the transmission of an ultrasonic wave.
Figure 5B:
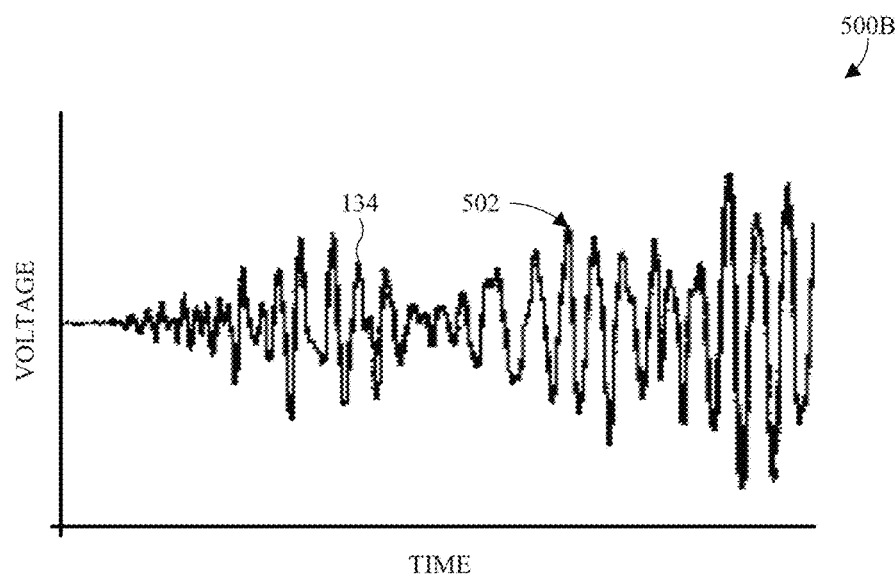
FIG. 5B illustrates a graph of some embodiments of a sensor signal generated by a receiving ultrasonic transducer.
Figure 5C:
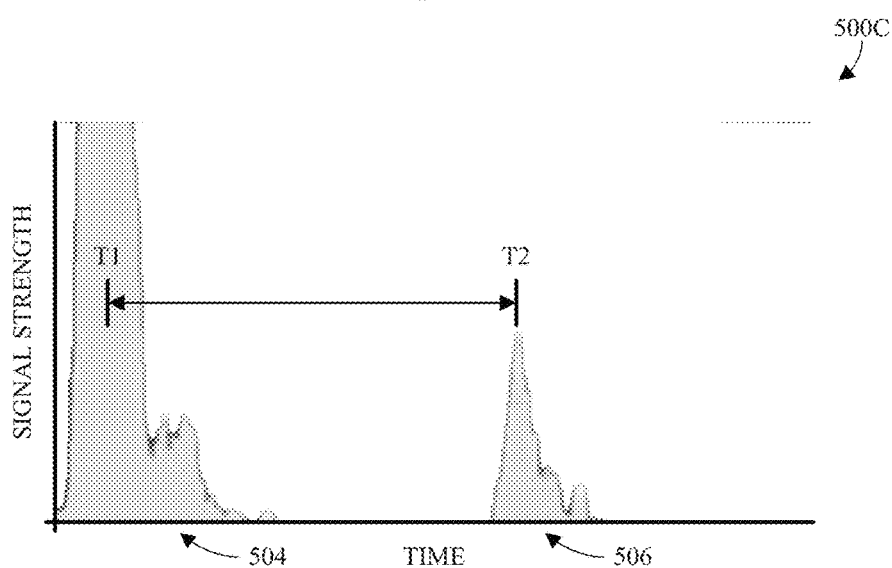
FIG. 5C illustrates a graph of some embodiments of signal strength for a sensor signal.

With reference to FIGS. 5A-C, graphical illustrations of some embodiments of the acts of the method of FIG. 4 are provided. Although FIGS. 5A-C are described in relation to the method, it will be appreciated that FIGS. 5A-C are not limited to the method, but instead may stand alone. Similarly, although the method is described in relation to FIGS. 5A-C, it will be appreciated that the method is not limited to the FIGS. 5A-C, but instead may stand alone.

FIG. 5A is a cross-sectional view 500A of some embodiments of a consumable element 102 and corresponds to some embodiments of Act 402. As illustrated, an ultrasonic wave 104 is transmitted towards a surface 130 on a front side 118 of the consumable element 102, from a transmitting ultrasonic transducer 124 over a back side 120 of the consumable element 102 that is opposite the front side 118. The ultrasonic wave 104 reflects off the front side surface 130, thereby resulting in a reflection 106 extending to a receiving ultrasonic transducer 126 over the back side 120 of the consumable element 102.

FIG. 5B is a graph 500B of some embodiments of a sensor signal 134 generated by the receiving ultrasonic transducer 126 (see FIG. 5A) and corresponds to some embodiments of Act 404. The dependent axis of the graph 500B corresponds to voltage (e.g., in volts), and the independent axis of the graph 500B corresponds to time (e.g., in microseconds). As illustrated, the sensor signal 134 is generated with electrical pulses 502 representing the ultrasonic wave 104 (see FIG. 5A) and the reflection 106 (see FIG. 5A) of the ultrasonic wave 104. Typically, the sensor signal 134 decays from the time the ultrasonic wave 104 is transmitted to the time the reflection 106 is received by the receiving ultrasonic transducer 126.

FIG. 5C is a graph 500C of some embodiments of signal strength for the sensor signal 134 (see FIG. 5B) and corresponds to some embodiments of Acts 408 and 410. The dependent access of the graph 500C corresponds to signal strength (e.g., in decibels), and the independent axis of the graph 500C corresponds to time (e.g., in microseconds). As illustrated, the graph 500C includes a first peak 504 for the ultrasonic wave 104 (see FIG. 5A) and a second peak 506 for the reflection 106 (see FIG. 5A) of the ultrasonic wave 104. Typically, the strength of the first peak 504 is greater than that of the second peak 506, since the sensor signal 134 typically decays over time. Further, as illustrated, the first and second peaks 504, 506 are identified and marked respectively at times T1 and T2.

Thus, as can be appreciated from above, the present disclosure provides a system for semiconductor manufacturing. A consumable element comprises a front side arranged inside a process chamber and a back side, opposite the front side, arranged outside the process chamber. An ultrasonic transducer is arranged on the back side of the consumable element, and is directed towards the front side of the consumable element. A monitoring unit is configured to estimate and monitor a remaining service lifetime of the consumable element using the ultrasonic transducer.

In other embodiments, the present disclosure provides a method for estimating and monitoring a remaining service lifetime of a consumable element of a process tool. An ultrasonic wave is transmitted towards a front side of a consumable element that is arranged in a process chamber, from a back side of the consumable element that is opposite the front side. A reflection time for the ultrasonic wave to traverse a thickness of the consumable element from the back side of the consumable element to the front side of the consumable element, and to reflect back to the back side of the consumable element from a surface on the front side of the consumable element, is measured. The reflection time is compared to a threshold indicative of an EOL of the consumable element.

In yet other embodiments, the present disclosure provides a system for semiconductor manufacturing. A plurality of consumable elements are arranged in one or more process chambers. Ultrasonic transducers correspond to the plurality of consumable elements. The ultrasonic transducers are arranged on back sides of the corresponding consumable elements, and focused towards front sides of the corresponding consumable elements, opposite the back sides. A monitoring unit is configured to estimate and monitor remaining service lifetimes of the consumable elements using the corresponding ultrasonic transducers.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A system for semiconductor manufacturing, the system comprising:
  a consumable element comprising a front side arranged inside a process chamber and a back side, opposite the front side, arranged outside the process chamber;
  a back plate arranged over and contacting the back side of the consumable element, wherein a fluid cavity is between the back plate and the consumable element;
  a magnetron arranged in the fluid cavity, between the back plate and the consumable element, wherein the magnetron is sunken into the back side of the consumable element;
  an ultrasonic transducer arranged on the back side of the consumable element, and directed towards the front side of the consumable element; and a monitoring unit configured to estimate and monitor a remaining service lifetime of the consumable element using the ultrasonic transducer.

2. The system according to claim 1, wherein the consumable element is a physical vapor deposition (PVD) target.

3. The system according to claim 1, wherein the ultrasonic transducer is spaced from the consumable element.

4. The system according to claim 1, wherein the ultrasonic transducer is directed towards regions on the front side of the consumable element where magnetic fields from the magnetron are strongest.

5. The system according to claim 1, further comprising: a fluid arranged in the fluid cavity, wherein the ultrasonic transducer is arranged in an opening extending through the back plate and arranged in direct communication with the fluid.

6. The system according to claim 1, further including: a pulser-receiver unit configured to transmit an ultrasonic wave towards the front side of the consumable element, and to receive a reflection of the ultrasonic wave off a surface on the front side of the consumable element, using the ultrasonic transducer.

7. The system according to claim 6, further comprising: a plurality of ultrasonic transducers including a transmitting ultrasonic transducer and a receiving ultrasonic transducer, wherein the ultrasonic transducer corresponds to the transmitting ultrasonic transducer or the receiving ultrasonic transducer, and wherein the pulser-receiver unit is further configured to transmit the ultrasonic wave using the transmitting ultrasonic transducer and to receive the reflection using the receiving ultrasonic transducer.

8. The system according to claim 6, wherein the monitoring unit is further configured to receive a sensor signal carrying electrical pulses representing the ultrasonic wave and the reflection, and to calculate a reflection time for the ultrasonic wave as a time difference between the electrical pulses.

9. The system according to claim 8, wherein the monitoring unit is further configured to transform the reflection time to a thickness estimate of the consumable element.

10. A system for semiconductor manufacturing, the system comprising:
a plurality of consumable elements removably mounted on one or more process chambers having corresponding back plates, wherein the back plates have ultrasonic transducer openings;
ultrasonic transducers corresponding to the plurality of consumable elements, wherein the ultrasonic transducers are arranged within the ultrasonic transducer openings over the corresponding consumable elements, wherein an ultrasonic transducer has an ultrasonic transducer bottom surface that is parallel with a back plate bottom surface of a back plate, and wherein the ultrasonic transducers are focused towards front sides of the corresponding consumable elements, opposite back sides of the corresponding consumable elements;
a plurality of magnetrons arranged in fluid cavities, between the back plates and the corresponding consumable elements, wherein a magnetron of the plurality of magnetrons is sunken into a back side of a corresponding one of the consumable elements; and
a monitoring unit configured to estimate and monitor remaining service lifetimes of the consumable elements using the corresponding ultrasonic transducers.

11. The system according to claim 10, further comprising: a plurality of process tools within which the consumable elements are arranged, and wherein the monitoring unit is central to the plurality of process tools.

12. The system according to claim 10, further comprising: a pulser-receiver unit configured to transmit ultrasonic waves towards the front sides of the consumable elements, and to receive reflections of the ultrasonic waves off surfaces on the front sides of the consumable elements, using the ultrasonic transducers, wherein the pulser-receiver unit is shared by the ultrasonic transducers, and wherein the monitoring unit is configured to estimate and monitor the remaining service lifetimes of the consumable elements based on reflection times of the ultrasonic waves.

13. The system according to claim 10, further comprising: a plurality of pulser-receiver units configured to collectively transmit ultrasonic waves towards the front sides of the consumable elements, and to collectively receive reflections of the ultrasonic waves off surfaces on the front sides of the consumable elements, using the ultrasonic transducers, wherein the monitoring unit is configured to estimate and monitor the remaining service lifetimes of the consumable elements based on reflection times of the ultrasonic waves, and wherein the monitoring unit is shared by the pulser-receiver units.

14. A system for semiconductor manufacturing, the system comprising:
a physical vapor deposition (PVD) process tool comprising:
a process chamber;
a PVD target comprising a front side that is inside the process chamber and that defines a top surface of the process chamber, and further comprising a back side that is opposite the front side and that is outside the process chamber, wherein the PVD target comprises a fluid cavity that is spaced over the top surface of the process chamber and that is sunken into the back side of the PVD target, such that the fluid cavity is below a top surface of the PVD target;
a back plate covering and contacting the back side of the PVD target, wherein the fluid cavity is between the back plate and the PVD target;
an ultrasonic transducer within an opening in the back plate, and directed towards the front side of the PVD target, wherein a bottom surface of the ultrasonic transducer is in fluid communication with the fluid cavity, and wherein a top surface of the ultrasonic transducer is not in fluid communication with the fluid cavity; and
a monitoring unit configured to estimate and monitor a remaining service lifetime of the PVD target using the ultrasonic transducer.

15. The system according to claim 14, wherein the back plate seals the fluid cavity, and wherein the PVD process tool further comprises a magnetron in the fluid cavity.

16. The system according to claim 15, wherein the back plate comprises a transducer opening that is directly over the fluid cavity and that opens into the magnetron opening, wherein the ultrasonic transducer is in the transducer opening, and wherein the PVD process tool further comprises a transducer seal sealing the transducer opening around the ultrasonic transducer.

17. The system according to claim 14, wherein a thickness of the PVD target varies laterally from side to side, and wherein the thickness of the PVD target is a vertical distance from a bottom surface of the PVD target to an interface between the PVD target and the back plate.

18. The system according to claim 17, wherein the ultrasonic transducer is arranged directly over a location on the bottom surface of the PVD target that has a smallest thickness.

19. The system according to claim 14, further comprising:
a pulser-receiver unit configured to transmit an ultrasonic wave towards a bottom surface of the PVD target, and to receive a reflection of the ultrasonic wave off the bottom surface of the PVD target, wherein the pulser-receiver unit is further configured to transmit the ultrasonic wave or receive the reflection of the ultrasonic wave through the ultrasonic transducer, and wherein the monitoring unit is configured to estimate and monitor the remaining service lifetime of the PVD target based on a time between transmitting the ultrasonic wave and receiving the reflection of the ultrasonic wave.

20. The system according to claim 14, further comprising:
a magnetron arranged in the fluid cavity, wherein the magnetron is sunken into the back side of the PVD target, such that a top surface of the magnetron is below an interface between the back plate and the PVD target.

* * * * *